United States Patent
Kanai et al.

(10) Patent No.: US 9,903,843 B2
(45) Date of Patent: Feb. 27, 2018

(54) FLOW CHANNEL MODULE AND CHROMATOGRAPH PROVIDED WITH THE FLOW CHANNEL MODULE

(71) Applicant: SHIMADZU CORPORATION, Kyoto-shi, Kyoto (JP)

(72) Inventors: Masaki Kanai, Kyoto (JP); Satoshi Matsuoka, Kyoto (JP); Masanori Nishino, Kyoto (JP); Takahiro Nishimoto, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 193 days.

(21) Appl. No.: 14/433,717

(22) PCT Filed: Oct. 19, 2012

(86) PCT No.: PCT/JP2012/077159
§ 371 (c)(1),
(2) Date: Apr. 6, 2015

(87) PCT Pub. No.: WO2014/061160
PCT Pub. Date: Apr. 24, 2014

(65) Prior Publication Data
US 2015/0233872 A1    Aug. 20, 2015

(51) Int. Cl.
*G01N 30/02* (2006.01)
*G01N 33/00* (2006.01)
*G01N 33/18* (2006.01)

(52) U.S. Cl.
CPC ......... *G01N 30/02* (2013.01); *G01N 33/0009* (2013.01); *G01N 33/1893* (2013.01); *Y10T 137/598* (2015.04)

(58) Field of Classification Search
CPC ............... G01N 30/02; G01N 33/1893; G01N 33/0009; Y10T 137/598
See application file for complete search history.

(56) References Cited

U.S. PATENT DOCUMENTS 5,569,365 A * 10/1996 Rabin ................... G01N 30/96
                                                                 204/450
6,612,153 B2    9/2003 White et al.
(Continued)

FOREIGN PATENT DOCUMENTS

JP    2005-43188 A    2/2005
JP    2011-89853 A    5/2011

OTHER PUBLICATIONS

International Search Report dated Jan. 22, 2013, issued in corresponding application No. PCT/JP2012/077159.
(Continued)

*Primary Examiner* — Paul West
*Assistant Examiner* — Xin Zhong
(74) *Attorney, Agent, or Firm* — Westerman, Hattori, Daniels & Adrian, LLP

(57) ABSTRACT

A flow channel module comprises a flow channel plate, a flow channel connection block, and a pressing mechanism. The flow channel plate is provided with a main body and a protrusion section protruding in the circumferential direction from the peripheral edge of the main body, the protrusion section having a port communicating with an inner flow channel. The flow channel connection block is provided with a concave section for being engaged with the protrusion section and having inside a port facing surface for facing the port, and an outer flow channel connection section that is connected to the port facing surface by a flow channel. The pressing mechanism is configured to press the protrusion section inserted in the concave section and the port facing surface against each other so that the flow channel and the port are connected while maintaining air tightness or liquid tightness.

8 Claims, 8 Drawing Sheets

(56) References Cited

U.S. PATENT DOCUMENTS

| | | |
|---|---|---|
| 7,273,517 B1 | 9/2007 | Lewis et al. |
| 2003/0080562 A1 | 5/2003 | Bailey et al. |
| 2004/0079696 A1 | 4/2004 | Hernandez |
| 2012/0135446 A1* | 5/2012 | Collins ............. B01L 3/502776 435/29 |
| 2012/0284991 A1* | 11/2012 | Kusz ..................... A61M 39/10 29/428 |
| 2015/0107993 A1* | 4/2015 | Izquierdo ................ C12Q 1/02 204/403.01 |

OTHER PUBLICATIONS

Nishino et al., "Development of μGC (Micro Gas Chromatography) with High Performance Micromachined Chip Column", IEEJ Trans, 2009, pp. 358-364, vol. 4.

* cited by examiner

FLOW CHANNEL MODULE AND CHROMATOGRAPH PROVIDED WITH THE FLOW CHANNEL MODULE

TECHNICAL FIELD

The present invention relates to a flow channel module, and a chromatograph, such as a gas chromatograph or a liquid chromatograph, using the flow channel module as an analytical column.

BACKGROUND ART

Conventionally, much research on forming of a fine flow channel structure, and synthesis, separation, analysis, and the like of fluid samples in the flow channel has been conducted, and a micro TAS (Total Analysis System) is widely known in its technical field. As a method of forming a fine flow channel structure, a method of joining two plates to form a flat flow channel plate is generally known. One of the flow channel plates has a groove to be a fine flow channel formed on its surface, and the other plate has through holes formed at positions corresponding to the end portions of the fine flow channel as an outlet and an inlet of the fine flow channel, and the plates are joined with the surface on which the groove is formed arranged on the inside.

To transfer a fluid sample into and out of such a flow channel plate, high air tightness or liquid tightness has to be secured at the time of connecting an outer flow channel to the inner flow channel of the flow channel plate so that there is no leakage of the fluid sample. When connecting an outer flow channel to the inner flow channel of the flow channel plate, it is desired that, in addition to there being no leakage of a fluid sample from the connection section, the dead volume at the connection section is small. For example, in the case of using the flow channel plate as a column for separation/analysis such as a gas chromatography or a liquid chromatography, if there is a great dead volume at the connection section especially at the outlet side, the peak shape of the chromatogram is affected, and the analysis result is impaired.

As methods of preventing leakage of a fluid sample at the connection section, and of reducing the dead volume at the connection section, a method of pressing, against a flow channel plate main body, a connection block to which a capillary or the like which is an outer flow channel may be connected by using a ferrule, with a gasket sandwiched between the connection block and the flow channel plate (see Patent Document 1), and a method of joining a connection block directly to a flow channel plate main body (see Non-Patent Document 1), may be cited.

PRIOR ART DOCUMENTS

Patent Document

Patent Document 1: U.S. Pat. No. 6,612,153

Non-Patent Document

Non-Patent Document 1: Nishino M, et al. Development chip of μGC (Micro Gas Chromatography) with high performance micromachined chip column, IEEJ Trans, 4, pp 358-364,(2009)

SUMMARY OF THE INVENTION

Problems to be Solved by the Invention

In the case of adopting the method of pressing a connection block against the surface of a flow channel plate main body, the connection block has to be pressed hard against the flow channel plate so that there is no leakage from between the connection block and the flow channel plate. The flow channel plate has a thin thickness, and when a part thereof is pressed hard, the flow channel plate may be distorted. Accordingly, a backing plate is arranged on the surface of the flow channel plate opposite the surface against which the connection block is to be pressed, and the connection block is pressed against the flow channel plate with the flow channel plate sandwiched between the connection block and the backing plate.

However, if the backing plate is not arranged parallel to the connection block, the connection block comes into partial contact with the flow channel plate, and the air tightness or the liquid tightness between the flow channel plate and the connection block is not secured, and a fluid sample will leak from the connection section. To prevent such a problem, a retaining mechanism for arranging the connection block and the backing plate in parallel with each other becomes necessary, and the mechanism for connecting the outer flow channel to the inner flow channel of the flow channel plate becomes large.

On the other hand, in the case of adopting the method of directly joining the connection block to the flow channel plate main body, there is no concern regarding leakage from the connection section between the connection block and the flow channel plate. However, as can also be said for the method described above of pressing the connection block against the surface of the flow channel plate, the connection block becomes a protrusion protruding from the surface of the flow channel plate, and thus, in the case of attaching a heating mechanism to the flow channel plate, a flat heater cannot be adhered to the entire surface of the flow channel plate main body as it is due to the presence of the connection block, and the heater has to be processed. Also, the flow channel plate main body will not have a simple flat shape and will have a protrusion, and attachment/detachment of the heater and the flow channel plate will be burdensome.

Furthermore, in either of the methods described above, the heat capacity of the flow channel plate main body is not uniform across the surface due to the presence of the connection section on the flow channel plate main body, and at the time of heating the flow channel plate main body by the heater, it is difficult to make the temperature of the heater uniform across the surface. If the temperature of the flow channel plate main body is not uniform across the surface, the temperature of the inner flow channel will be different depending on the position, and use in a case where the influence of temperature is strongly felt as in the case of synthesis reaction or chromatography is not possible.

Accordingly, the present invention has its aim to secure high air tightness and liquid tightness at a connection section between an inner flow channel of a flow channel plate and an outer flow channel, and also, to enable uniform heating across the surface of a flow channel plate main body.

Solutions to the Problems

A flow channel module according to the present invention comprises a flow channel plate including, at a flat flow channel plate main body having a main plane and on the main plane, a protrusion section protruding in a circumferential direction from a peripheral edge of the flow channel plate main body, where an inner flow channel is formed in the flow channel plate main body and an end portion of the inner flow channel is drawn into the protrusion section, and where a port communicating with the inner flow channel is provided to a surface of the protrusion section, a flow channel connection block including a concave section for being engaged with the protrusion section and having inside a port facing surface for facing the port of the protrusion section, and an outer flow channel connection section that is connected to the port facing surface by a flow channel, and a pressing mechanism for pressing the protrusion section inserted in the concave section and the port facing surface against each other so that the flow channel that connects the port facing surface and the outer flow channel connection section and the port are connected while maintaining air tightness or liquid tightness.

Additionally, to "press the protrusion section and the port facing surface against each other" refers not only to a case of bringing into direct contact and pressing against each other the surface of the protrusion section where the port is provided and the port facing surface, but also to a case of pressing the two against each other while sandwiching an elastic sealing member such as a gasket between the two.

A gas chromatograph according to the present invention comprises an analytical column composed of the flow channel module of the present invention, a sample injection section connected to a port on an inlet side of the analytical column via a flow channel, for injecting a sample gas into the analytical column, and a detector connected to a port on an outlet side of the analytical column via a flow channel, for detecting a sample component separated by the analytical column.

Effects of the Invention

According to the flow channel module of the present invention, the protrusion section provided to the flow channel plate main body is inserted into the concave section of the flow channel connection block and is connected to an outer flow channel, and thus, the outer flow channel may be connected to the port of the flow channel plate without interfering with the flat flow channel plate main body of the flow channel plate. Temperature control of the flow channel plate main body using a flat heater is thereby enabled without forming a protruding structure to the flow channel plate main body. Also, since the pressing mechanism for pressing the port of the protrusion section inserted in the concave section and the port facing surface inside the concave section against each other is provided to the flow channel connection block, the air tightness or the liquid tightness at the connection section of the inner flow channel of the flow channel plate and the connection flow channel of the flow channel connection block may be improved. Since the concave section is provided in such a way as to be engaged with the protrusion section, positioning of the port of the protrusion section and the outer flow channel connection section is easy. With this structure, the port of the protrusion section and the flow channel communicating with the outer flow channel connection section may be directly connected inside the concave section, and thus, an excess space does not have to be provided at the connection portion between the port of the protrusion section and the outer flow channel connection section, and the dead volume may be reduced.

According to the gas chromatograph of the present invention, the flow channel module of the present invention is used as the analytical column, and thus, the temperature of the analytical column is uniformly controlled, and also, high air tightness is maintained at the connection section of the flow channel at the analytical column, and the analysis result is highly reproducible.

BRIEF DESCRIPTION OF THE DRAWINGS

FIG. 1A is a plan view from above, and FIG. 1B is a cross-sectional view at the position of X-X in FIG. 1A.

EMBODIMENTS OF THE INVENTION

Figure 1A:
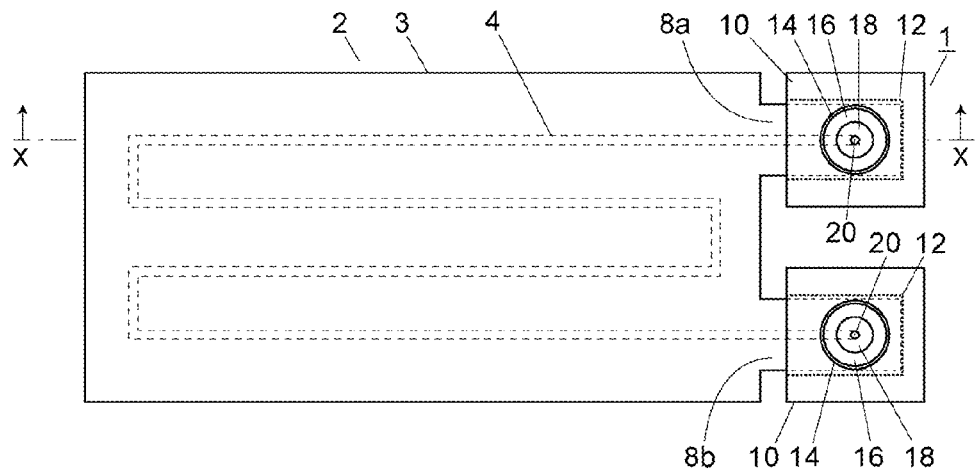
FIGS. 1A and 1B are diagrams showing an embodiment of a flow channel module, where

According to a flow channel module of the present invention, a flow channel connection block may be composed of a block main body and a movable section attached to the block main body. In this case, a concave section may be provided to the block main body, an outer flow channel connection section may be provided to the movable section, the block main body may be provided with a movable section insertion hole which is a hole for inserting the movable section and which penetrates from the surface of the block main body to the concave section, the movable section may be provided with an insertion section that is to be inserted from the tip end into the movable section insertion hole and a tip plane that is provided to the tip end of the insertion section, where the tip plane and the outer flow channel connection section are connected by a flow channel to form a port facing surface, and a pressing mechanism may have a thread tapped on the inner circumferential surface of the movable section insertion hole and a thread tapped on the outer circumferential surface of the insertion section for being screwed with the thread on the inner circumferential surface of the movable section insertion hole, and may press the tip plane against a protrusion section by relatively rotating the movable section with respect to the block main body and displacing the movable section in an insertion direction into the movable section insertion hole. According to such a structure, the structure of the flow channel connection block may be simplified, and the structure of the pressing mechanism may also be simplified. The air tightness or the liquid tightness at the connection section of the inner flow channel of the flow channel plate and a connection flow channel of the flow channel connection block is secured simply by inserting the protrusion section of the flow channel plate into the concave section of the block main body and rotating the movable section, and thus, the outer flow channel may be easily connected to the inner flow channel of the flow channel plate.

Furthermore, as another example of a case where the flow channel connection block of the present invention is structured from the block main body and the movable section, an example may be cited where the concave section and the outer flow channel connection section are provided to the block main body, the block main body is provided with the movable section insertion hole which is a hole for inserting the movable section and which penetrates from the surface of the block main body to an inner wall surface of the concave section facing the port facing surface, the movable section is provided with a plane at the tip end to be inserted into the movable section insertion hole, and a thread is tapped on the inner circumferential surface of the movable section insertion hole and a thread for being screwed with the thread on the inner circumferential surface of the movable section insertion hole is tapped on the outer circumferential surface of the movable section, and the pressing mechanism presses the protrusion section against the port facing surface by the plane at the tip end of the movable section by relatively rotating the movable section with respect to the block main body and displacing the movable section in an insertion direction into the movable section insertion hole. Also according to such a structure, the structure of the flow channel connection block and the structure of the pressing mechanism may be simplified. The air tightness or the liquid tightness at the connection section of the inner flow channel of the flow channel plate and a connection flow channel of the flow channel connection block is secured simply by inserting the protrusion section of the flow channel plate into the concave section of the block main body and rotating the movable section, and thus, the outer flow channel may be easily connected to the inner flow channel of the flow channel plate.

Also, the positional relationship between a terminal end wall surface at the deepest position inside the concave section and the end portion of the connection flow channel on the side of the port facing surface preferably corresponds to the positional relationship between a terminal end portion of the protrusion section and the port, and is preferably set so that positioning between the connection flow channel and the port is performed when the terminal end portion of the protrusion section that is inserted into the concave section comes into contact with the terminal end wall surface of the concave section. Then, the end portion of the connection flow channel on the side of the port facing surface is positioned with respect to the port simply by inserting the protrusion section of the flow channel plate deep into the concave section, and connection of the inner flow channel of the flow channel plate and the outer flow channel may be performed easily and accurately.

To increase the sealability at the connection portion of the flow channel at the flow channel connection block, it is conceivable to sandwich a ring sealing member having a through hole at a position corresponding to the port between the port of the protrusion section and the port facing surface; however, in this case, a concave section having the same shape as the sealing member is preferably provided at a position of the protrusion section where the sealing member is arranged. By this, positioning of the sealing member with respect to the port of the protrusion section is facilitated, and further, shifting of the position of the sealing member at the time of insertion of the protrusion section into the concave section of the flow channel connection block may be prevented.

The flow channel plate is preferably made of metal. The flow channel plate will then have high strength, and the force of pressing by the pressing mechanism of the flow channel connection block may be increased, and the sealability at the connection section of the flow channel at the flow channel connection block may be further increased.

Moreover, a stationary phase for chromatogram separation may be supported in the inner flow channel of the flow channel plate. The flow channel module of the present invention may then be used as an analytical column for chromatography.

Figure 1B:
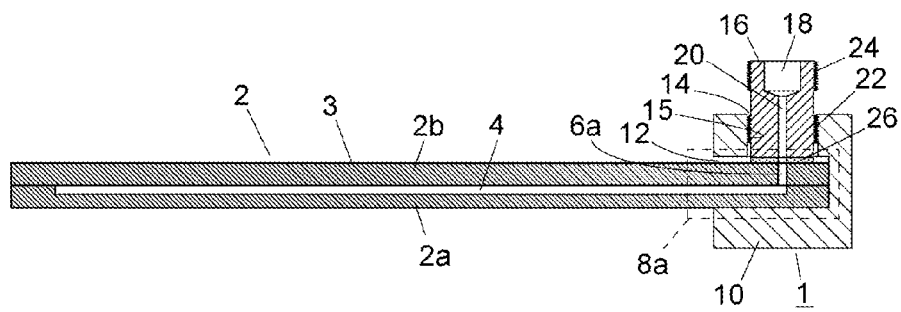

An embodiment of a flow channel module will be described with reference to FIGS. 1A and 1B.

Figure 3:
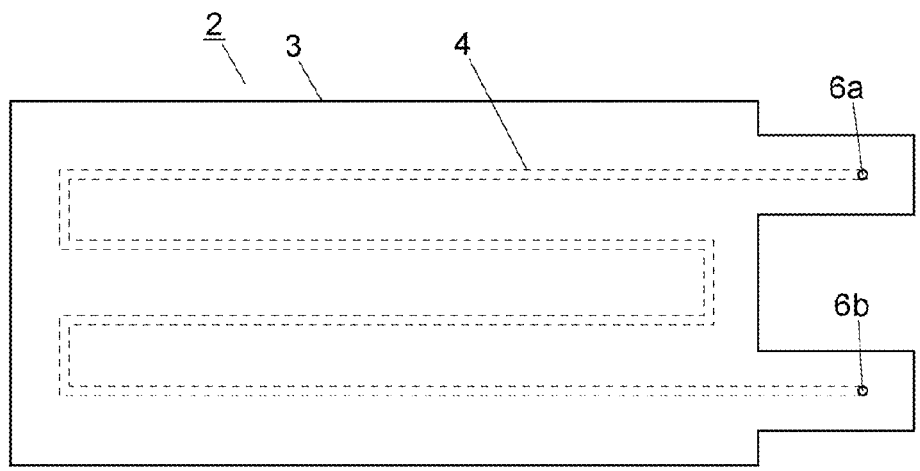
FIG. 3 is a plan view showing a flow channel plate of the embodiment.

This flow channel module is composed of a flow channel plate 2, flow channel connection blocks 1, and a pressing mechanism. The flow channel plate 2 is composed of a flow channel plate main body 3, and protrusion sections 8a and 8b. The flow channel plate 2 is structured by joining a plate 2a made of metal (for example, a stainless steel) on which a groove to be a flow channel 4 is formed on one surface and a metal plate 2b to which through holes to be ports 6a and 6b (see FIG. 3) for communicating with the flow channel 4 are formed. The flow channel plate 2 includes the flow channel plate main body 3, which has most of the flow channel 4 formed therein, and the two protrusion sections 8a and 8b protruding in the circumferential direction from the peripheral edge of the flow channel plate main body. Both end portions of the flow channel 4 are drawn near the terminal end portions inside the protrusion sections 8a and 8b, respectively. The ports 6a and 6b, which communicate with respective end portions of the flow channel 4, are provided to one surface of the protrusion sections 8a and 8b. The thickness of the plates 2a and 2b is, for example, 0.5 mm. The groove of the plate 2a is, for example, 200 μm in width and 100 μm in depth, and is formed by, for example, photo-etching. The diameter of the through holes of the plate 2b is, for example, 0.5 mm.

Both the ports 6a and 6b of the flow channel plate 2 are connected to outer flow channels by the flow channel connection blocks 1. The flow channel connection blocks 1 are attached respectively to the protrusion sections 8a and 8b of the flow channel plate 2, and connect capillaries as outer flow channels to the respective ports 6a and 6b. The flow channel connection blocks 1 attached to the protrusion sections 8a and 8b have the same structure. In the following, only the flow channel connection block 1 attached to the protrusion section 8a will be described.

Figure 2:
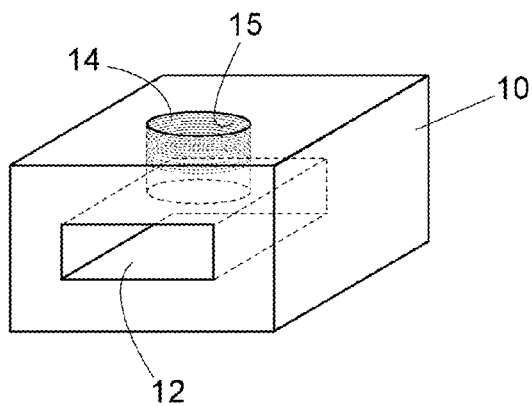
FIG. 2 is a perspective view showing a block main body of a flow channel connection block of the embodiment.

The flow channel connection block 1 is composed of a block main body 10, and a retainer 16. As shown in FIG. 2, the block main body 10 is a cube-shaped member. The block main body 10 includes a concave section 12, which has an opening to one side surface of the block main body 10, for inserting and engaging with the protrusion section 8a of the flow channel plate 2. A circular hole 14 that reaches the concave section 12 and that meets the concave section 12 perpendicularly is opened to a surface perpendicular to the side surface to which the opening of the concave section 12 is opened. The hole 14 is a movable section insertion hole into which the retainer 16 is to be inserted to be attached, and has a thread 15 for attaching/detaching the retainer 16 by fastening of a screw tapped on the inner circumferential surface. As will be described later, a thread for being screwed with the thread on the inner circumferential surface of the hole 14 is tapped on the outer circumferential surface of the retainer 16.

The retainer 16 is a columnar member. One end of the retainer 16 is the insertion section that is to be inserted into the hole 14 of the block main body 10, and the other end is the outer flow channel connection section for connecting a capillary, which is an outer flow channel. The end portion of the one end of the retainer 16 is a plane (a tip plane). When this plane is inserted into the hole 14 of the block main body 10 and faces the space inside the concave section 12, it faces a surface of the protrusion section 8a of the flow channel plate 2 that is inserted in the concave section 12. The protrusion section 8a is inserted into the concave section 12 with the surface on the side of the port 6a facing the side of the hole 14 inside the concave section 12. The plane of the one end of the retainer 16 is the port facing surface that faces the port 6a of the protrusion section 8a.

On the outer circumferential surface near the one end, a thread 22 that is to be screwed with the thread 15 on the inner circumferential surface of the hole 14 is tapped. The retainer 16 is to be displaced in the axial direction (in FIG. 1A, the perpendicular direction to the plane of the sheet, and in FIG. 1B, the up-down direction) with respect to the block main body 10 by being rotated. The retainer 16 forms the movable section of the flow channel connection block 1, and the thread 15 tapped on the inner circumferential surface of the hole 14 and the thread 22 tapped on the outer circumferential surface of the retainer 16 form a movable section displacement mechanism.

An opening 18 for connecting a capillary is provided to an end portion at the other end of the retainer 16, and the opening 18 communicates with the plane at the one end portion through the connection flow channel 20. A thread 24 for fixing the capillary to the retainer 16 by a ferrule is tapped on the outer circumferential surface on the other end of the retainer 16.

The position of the end portion of the connection flow channel 20 on the side of the port facing surface in a state where the retainer 16 is attached to the block main body 10 is a position corresponding to the position of the port 6a when the terminal end portion of the protrusion section 8a inserted in the concave section 12 is at the terminal end wall surface at the deepest position in the concave section 12. Accordingly, positioning of the connection flow channel 20 and the port 6a is automatically performed by simply inserting the protrusion section 8a into the deepest position in the concave section 12.

The protrusion section 8a of the flow channel plate 2 is inserted into the concave section 12 of the block main body 10 while having a gasket 26 mounted on a portion where the port 6a is provided. The gasket 26 is a sealing member of elastic material, such as nickel, copper, stainless steel, polytetrafluoroethylene, or polyimide, having a through hole with the same inner diameter as the port 6a at the center portion, and is interposed between the plane at the tip end of the retainer 16 (the port facing surface) and the protrusion section 8a inside the concave section 12. The thickness of the gasket 26 is, for example, 500 μm.

By rotating the retainer 16 in the direction of displacement toward the back of the hole 14 (the concave section 12 side) in a state where the protrusion section 8a on which the gasket 26 is mounted is inserted in the concave section 12, the plane at an end portion of the retainer 16 is pressed against and adhered, via the gasket 26, to the plane of the portion of the protrusion section 8 where the port is provided, and the connection flow channel 20 and the port 6a are connected with a high level of air tightness. This structure forms the pressing mechanism for pressing the plane at an end portion of the retainer 16 and the protrusion section 8 against each other. In this embodiment, the flow channel plate 2 is composed of metal plates 2a and 2b having high strength, and the plane at the end portion of the retainer 16 may be pressed against the protrusion section 8 with high force by the pressing mechanism. Additionally, even when the flow channel plate 2 is composed of metal plates, the flow channel plate 2 may be used as an analytical column of a chromatograph by applying surface treatment, such as glass coating, on the surface of the inner flow channel 4. Such surface treatment will be described with reference to an embodiment of a gas chromatograph which will be described using FIG. 7.

Figure 5:
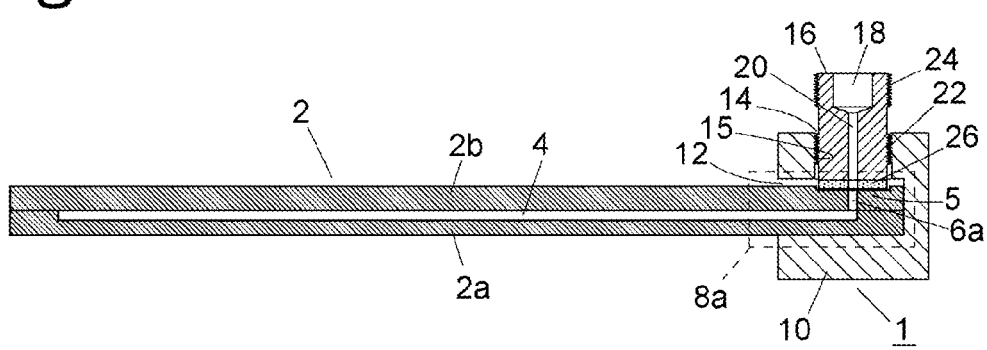
FIG. 5 is a cross-sectional view showing another embodiment of the flow channel module.

Additionally, as shown in FIG. 5, a recessed section 5 having the same shape as the gasket 26 and a depth of about 100 μm may be provided at the mounting position of the gasket 26 on the protrusion section 8a of the flow channel plate 2. By this, positioning of the gasket 26 with respect to the port 6a is facilitated, and shifting of the position of the gasket 26 may be prevented.

Figure 4:
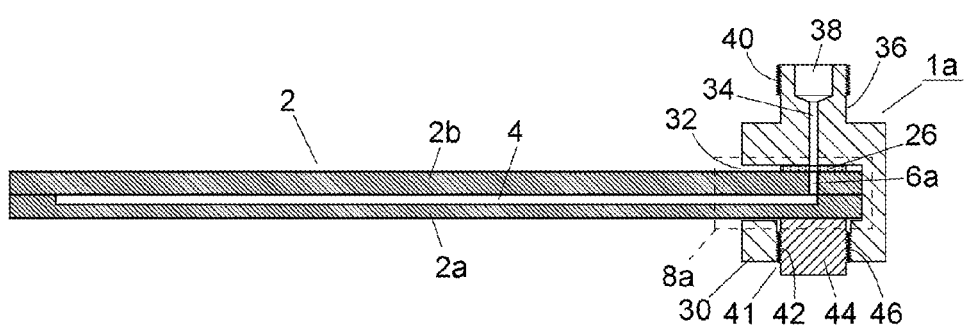
FIG. 4 is a cross-sectional view showing another embodiment of the flow channel module together with the flow channel plate.

Another embodiment of the flow channel connection block will be described with reference to FIG. 4.

A flow channel connection block 1a according to this embodiment is composed of a block main body 30 and a retainer 44. The block main body 30 includes an outer flow channel connection section 36. The outer flow channel connection section 36 protrudes in a columnar manner from one surface (the top surface in the drawing) of the block main body 30, and a thread 40 for fixing a capillary by a ferrule is tapped on its outer circumferential surface. An opening 38 for flow channel connection is provided inside the outer flow channel connection section 36, and the opening 38 communicates with the inside of a concave section 32 described later via a connection flow channel 34.

The block main body 30 includes the concave section 32 for inserting and engaging the protrusion section 8a of the flow channel plate 2. The concave section 32 includes an opening at one side surface of the block main body 30, and is provided at a direction orthogonal to the connection flow channel 34 inside the outer flow channel connection section 36. A circular hole 41 is opened on a surface of the block main body 30, opposite the outer flow channel connection section 36. The hole 41 reaches the concave section 32, and its end portion on the side of the concave section 32 faces an end portion of the connection flow channel 34.

The hole 41 is a movable section attaching hole for inserting and attaching the retainer 44, and a thread 42 is tapped on the inner circumferential surface of the hole 41. A thread for being screwed with the thread 42 tapped on the inner circumferential surface of the hole 41 is tapped on the outer circumferential surface of the retainer 44, and the retainer 44 may be displaced in the axial direction (in FIG. 4, the up-down direction) with respect to the block main body 30 by being fitted into the hole 41 and rotated. An end portion of the retainer 44 facing the concave section 32 is a plane that supports, within the concave section 32, a surface opposite the port 6a of the protrusion section 8a inserted in the concave section 32.

The retainer 44 forms a movable section, and the thread 42 tapped on the inner circumferential surface of the hole 41 and a thread 46 tapped on the outer circumferential surface of the retainer 44 form a movable section displacement mechanism. Also, this movable section displacement mechanism forms a pressing mechanism for pressing the plane of the protrusion section 8a, at a portion where the port 6a is provided, against a wall surface inside the concave section 32 where the connection flow channel 34 is provided by displacing the retainer 44 toward the back (the concave section 32 side) of the hole 41.

Figure 6:
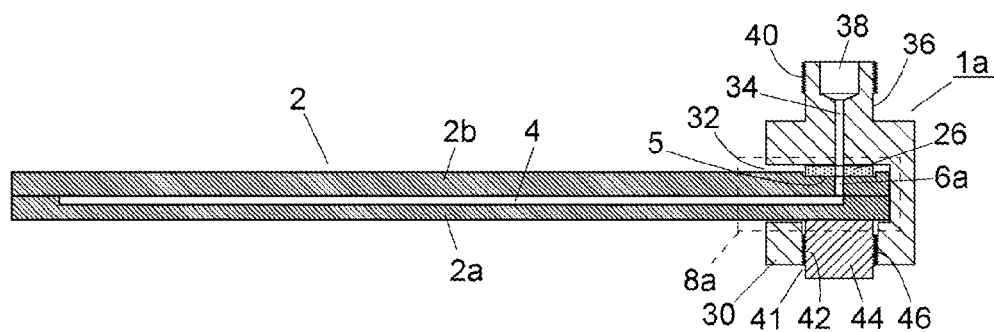
FIG. 6 is a cross-sectional view showing further another embodiment of the flow channel module.

Also in this embodiment, the gasket 26 is mounted at the portion of the port 6a of the protrusion section 8a that is inserted in the concave section 32, but by providing, as shown in FIG. 6, the recessed section 5 having the same shape as the gasket 26 and a depth of about 100 μm at the mounting position of the gasket 26 on the protrusion section 8a of the flow channel plate 2, positioning of the gasket 26 with respect to the port 6a is facilitated, and also, shifting of the position of the gasket 26 may be prevented.

Figure 8A:
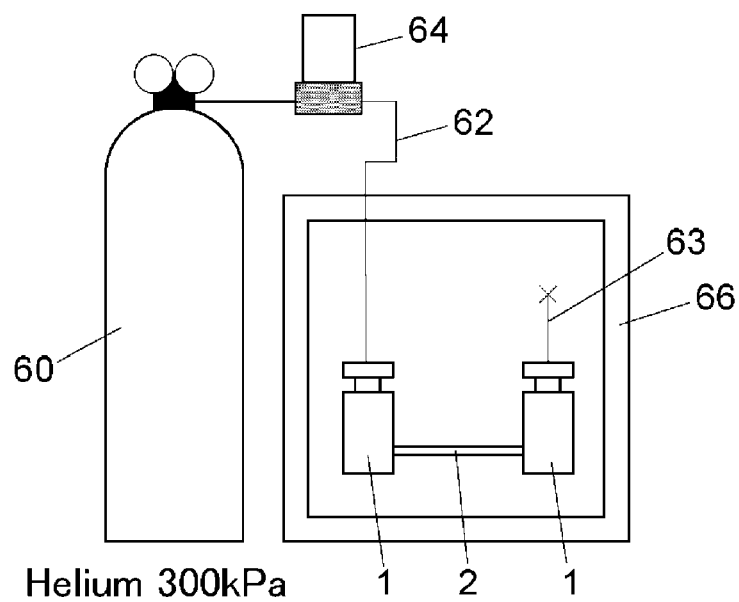
FIG. 8A is a diagram schematically showing the structure of an experimental device used for testing gas leakage at a connection section where a flow channel is connected by using the flow channel module of the embodiment in FIGS. 1A and 1B.

FIG. 8A is a diagram schematically showing the structure of an experimental device used at the time of testing fluid leakage where the outer flow channel is connected to the flow channel plate 2 using the flow channel connection block 1 described with reference to FIGS. 1(A), 1(B), 2 and 3. One end of a capillary 62 is connected, by using the flow channel connection block 1, to one of the ports 6a and 6b that communicate with the inner flow channel 4 of the flow channel plate 2, and a capillary 63 is similarly connected to the other port by using the flow channel connection block 1. A gas cylinder for supplying helium gas at 300 kPa via a flow sensor 64 is connected to the other end of the capillary 62, and the other end of the capillary 63 is closed. The flow channel plate 2 and the two flow channel connection blocks 1 are accommodated within an oven 66 whose internal temperature is controlled.

Figure 8B:
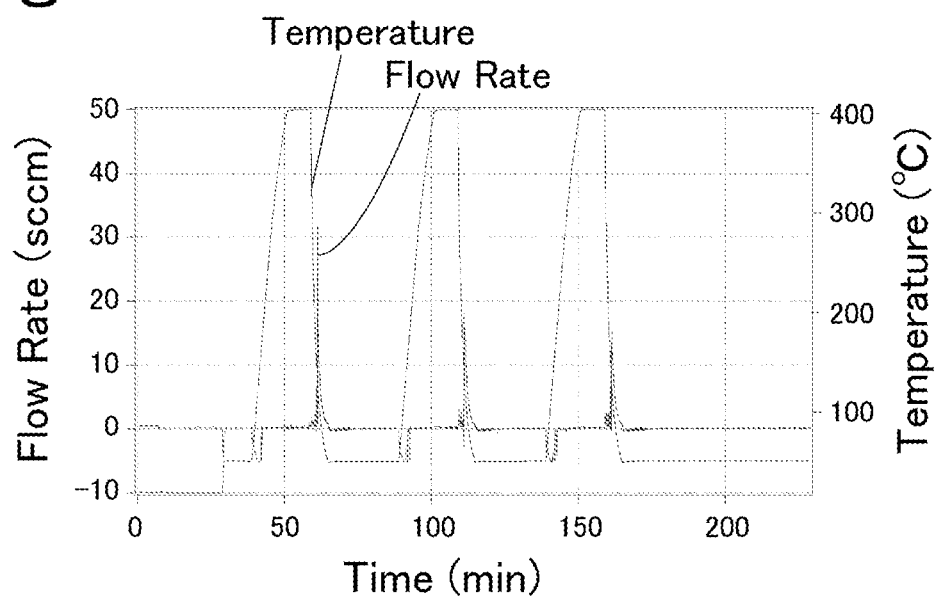
FIG. 8B is a graph showing the test result.

FIG. 8B is a graph showing the results of a test obtained by using the experimental device in FIG. 8A. In this test, the temperature within the oven 66 is periodically changed in the range of about 50° C. to about 400° C., and the rate of flow through the capillary 62 at the time is measured by the flow sensor 64. As shown in the graph, it is confirmed that, when the temperature inside the oven 66 is constant at about 50° C. or about 400° C., the flow rate is zero, and there is no leakage of helium gas at the connection section inside the flow channel connection block 1. Additionally, a flow rate change is detected by the flow sensor 64 when the temperature inside the oven 66 is drastically changed from about 50° C. to about 400° C., or from about 400° C. to about 50° C. This is due to the influence of heat expansion accompanying the drastic temperature change.

Figure 9A:
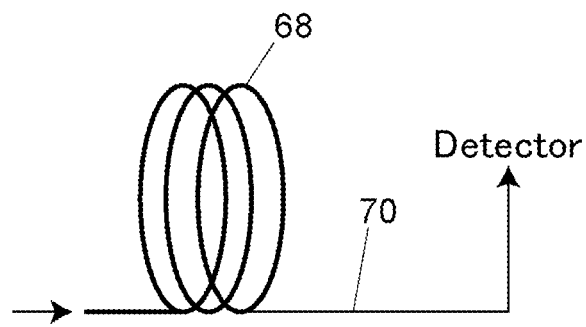
FIG. 9A is a diagram schematically showing the structure of a device used for testing the dead volume of the flow channel module of the embodiment in FIGS. 1A and 1B.
Figure 9B:
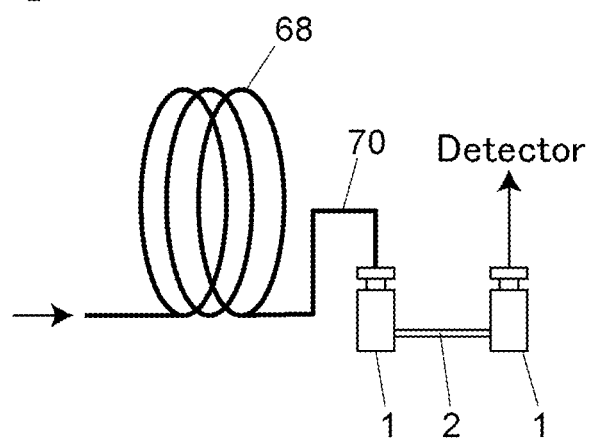
FIG. 9B is a diagram schematically showing the structure of a device used for the test.

FIGS. 9A and 9B schematically show an experimental device used at the time of performing a test regarding an increase in the dead volume due to the flow channel connection block. The experimental device in FIG. 9A is a regular gas chromatograph using a capillary column, and a flow channel 70 on the downstream of a capillary column 68 is connected to a detector. The experimental device in FIG. 9B has the flow channel 70 on the downstream of the capillary column 68 connected to a port on the inlet side of the flow channel plate 2 by the flow channel connection block 1, and a port on the outlet side of the flow channel plate 2 connected by the flow channel connection block 1 to a flow channel linked to a detector.

Figure 10:
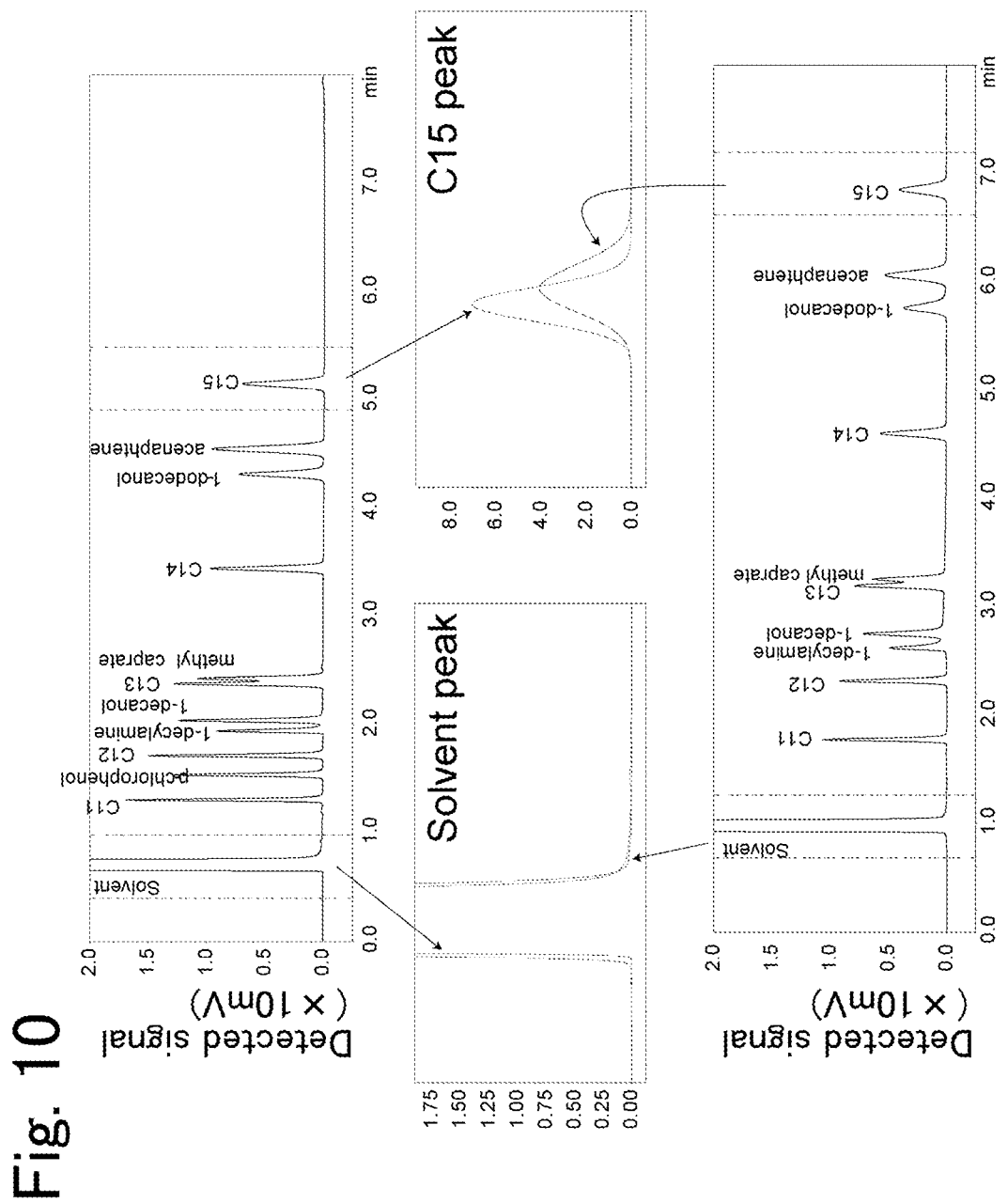
FIG. 10 is a graph showing the test result.

FIG. 10 shows chromatograms measured by using the experimental devices in FIGS. 9A and 9B. The chromatogram shown at the top was obtained by using the experimental device in FIG. 9A, and the chromatogram shown at the bottom was obtained by using the experimental device in FIG. 9B. The two waveforms in the middle (Solvent peak and C15 peak) are enlarged views of peak waveforms of the chromatograms at the top and the bottom for the same component.

If the dead volume inside the flow channel connection block 1 is great, the components separated by the capillary column 68 get mixed at the dead volume portion, and peak shapes of the chromatogram for the components should be greatly distorted. Comparing the two enlarged peak shapes, it can be seen that the peak shape of the chromatogram obtained by the experimental device in FIG. 9B is not distorted. Accordingly, it is confirmed that there is no great dead volume inside the flow channel connection block 1. Additionally, the peak shape obtained by the experimental device in FIG. 9B is lower in height and horizontally wider (in the time axis direction) than the peak shape obtained by the experimental device in FIG. 9A, and this is due to connection of a flow channel plate having an inner flow channel of a long flow channel length before the detector.

Figure 7:
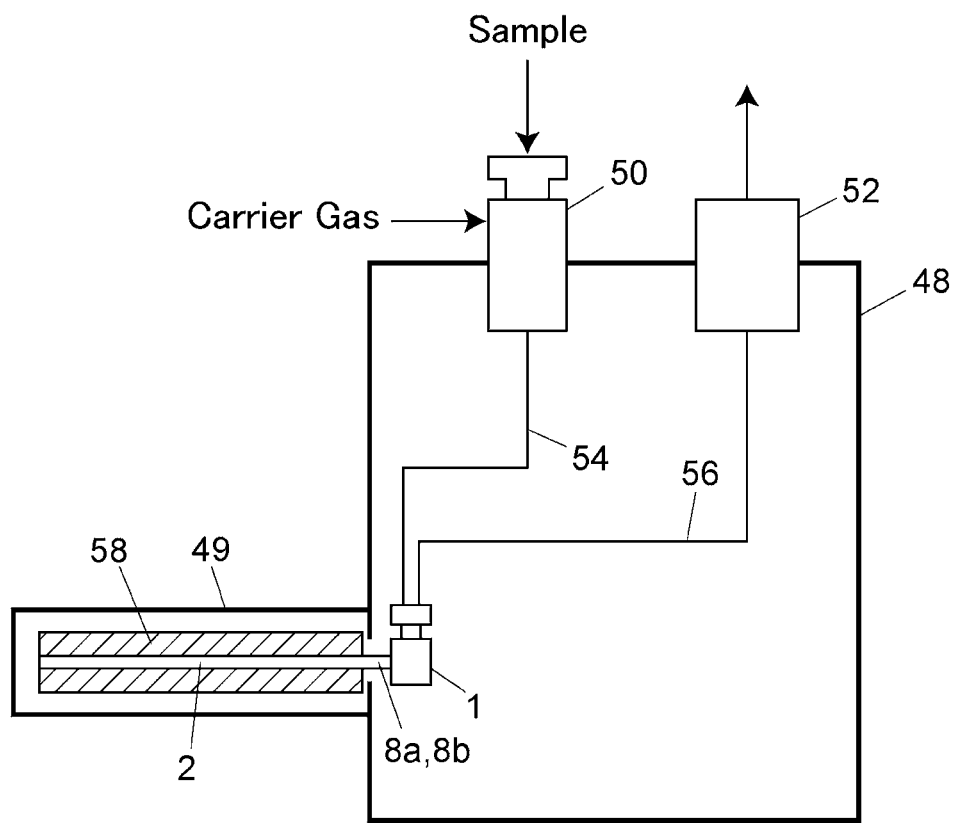
FIG. 7 is a structural diagram schematically showing an embodiment of a gas chromatograph.

Next, a gas chromatograph which is an example of an analysis device to which the flow channel connection block of the present invention is applied will be described with reference to FIG. 7. Additionally, according to this gas chromatograph, the flow channel connection block 1 described with reference to FIGS. 1(A), 1(B), 2 and 3 is used, but the flow channel connection block 1a described with reference to FIG. 4 may likewise be applied. Moreover, the flow channel plate 2 used by this gas chromatograph has the structure shown in FIG. 3. Surface treatment is applied on the inner surface of the inner flow channel 4 of the flow channel plate 2 to thereby obtain an analytical column. As an example of the surface treatment, first, the inner surface of the flow channel is covered by a glass passivated layer to prevent absorption of a sample by a metal oxide site. The passivated layer is a coated and crosslinked polysilazane. A silanol group of the passivated layer is terminated by a silylating agent, and therefore, a stationary phase such as polymethyl silicone having several functional groups is supported.

A sample injection section 50 is connected to an inlet port of the flow channel plate 2 via a capillary 54, and an outlet port of the flow channel plate 2 is connected to a detector 52 via a capillary 56. The sample injection section 50 is for injecting a gasified sample into the flow channel plate 2 by a carrier gas. A fine inner flow channel forming a separation column is present inside the flow channel plate 2, and the sample is separated into components in the inner flow channel. The detector 52 is for detecting each component of the sample separated by the inner flow channel of the flow channel plate 2, and, as an example, an FID detector is used. The flow channel plate 2 has the structure shown in FIG. 3 and includes a flow channel plate main body and protrusion sections 8a and 8b protruding in the circumferential direction from the peripheral edge of the flow channel plate main body.

The sample injection section 50 and the detector 52 are attached to the top portion of an oven 48 for controlling the internal temperature, and the capillaries 54 and 56 are accommodated inside the oven 48. A column module 49 accommodating inside the flow channel plate main body of the flow channel plate 2 is attached to a side wall of the oven 48. Inside the column module 49, the upper surface and the lower surface of the flow channel plate main body of the flow channel plate 2 are in contact with flat heaters 58, and the temperature of the flow channel plate 2 is controlled independently of the oven 48.

The column module 49 is attached with the flow channel plate 2 being horizontal in such a way that the protrusion sections 8a and 8b of the flow channel plate 2 are on the side of the oven 48. Openings are provided to a side surface of the column module 49 and a side wall of the oven 48 to draw the protrusion sections 8a and 8b of the flow channel plate 2 into the oven 48. The flow channel connection blocks 1 are attached to the protrusion sections 8a and 8b of the flow channel plate 2, and the capillaries 54 and 56 are connected respectively to ports 6a and 6b provided to the protrusion sections 8a and 8b by the flow channel connection blocks 1.

Figure 11:
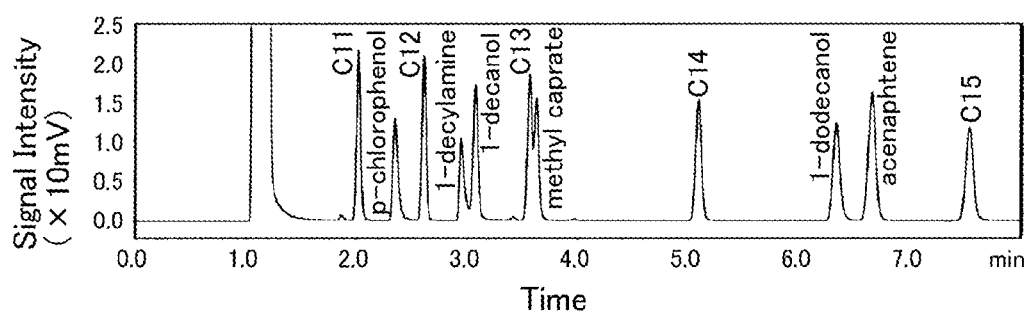
FIG. 11 is a chromatogram acquired by a gas chromatograph device according to the embodiment.

FIG. 11 shows an example of a chromatogram obtained by the gas chromatograph device. When calculating with respect to the C15 peak of this chromatogram, the number of theoretical plates was 57,000. Accordingly, it can be seen that when the flow channel plate 2 is used as an analytical column of a gas chromatograph, superior performance may be achieved.

DESCRIPTION OF REFERENCE SIGNS 1, 1a: Flow channel connection block
2: Flow channel plate
2a, 2b: Metal plate
4: Inner flow channel
5: Recessed section
6a, 6b: Port (flow channel plate)
8a, 8b: Protrusion section
10, 30: Block main body
12, 32: Concave section
14, 41: Hole (movable section attaching hole)
15, 22, 24, 40, 42, 46: Thread
16, 44: Retainer (movable section)
18, 38: Opening (for outer flow channel connection)
20, 34: Connection flow channel
26: Gasket (sealing member)
36: Outer flow channel connection section

What is claimed is:

1. A flow channel module comprising:
a flow channel plate including, at a flat flow channel plate main body having a main plane and on the main plane, a flat protrusion section protruding in a circumferential direction from a peripheral edge of the flow channel plate main body, where an inner flow channel is formed in the flow channel plate main body and an end portion of the inner flow channel is drawn into the protrusion section, and where a port communicating with the inner flow channel is provided to a flat surface of the protrusion section, wherein the flat surface, where the port is provided, is perpendicular to a tip end surface of the protrusion section;
a flow channel connection block including a concave section for being engaged with the protrusion section and having inside a port facing surface for facing the port of the protrusion section, and an outer flow channel connection section that is connected to the port facing surface by a flow channel; and
a pressing mechanism for pressing the protrusion section inserted in the concave section and the port facing surface against each other so that the flow channel that connects the port facing surface and the outer flow channel connection section and the port are connected while maintaining air tightness or liquid tightness.

2. The flow channel module according to claim 1, wherein the flow channel connection block includes a block main body and a movable section attached to the block main body,
wherein the concave section is provided to the block main body, and the outer flow channel connection section is provided to the movable section,
wherein the block main body is provided with a movable section insertion hole which is a hole for inserting the movable section and which penetrates from a surface of the block main body to the concave section,
wherein the movable section is provided with an insertion section that is to be inserted from a tip end into the movable section insertion hole and a tip plane that is provided to the tip end of the insertion section, where the tip plane and the outer flow channel connection section are connected by a flow channel to form the port facing surface, and
wherein the pressing mechanism includes a thread tapped on an inner circumferential surface of the movable section insertion hole and a thread tapped on an outer circumferential surface of the insertion section for being screwed with the thread on the inner circumferential surface of the movable section insertion hole, so that it presses the tip plane against the protrusion section by relatively rotating the movable section with respect to the block main body and displacing the movable section in an insertion direction into the movable section insertion hole.

3. The flow channel module according to claim 1, wherein the flow channel connection block includes a block main body and a movable section attached to the block main body,
wherein the concave section and the outer flow channel connection section are provided to the block main body,
wherein the block main body is provided with a movable section insertion hole which is a hole for inserting the movable section and which penetrates from a surface of the block main body to an inner wall surface of the concave section facing the port facing surface,
wherein the movable section is provided with a plane at a tip end that is to be inserted into the movable section insertion hole, and
wherein the pressing mechanism includes a thread tapped on an inner circumferential surface of the movable section insertion hole and a thread tapped on an outer circumferential surface of the movable section for being screwed with the thread on the inner circumferential surface of the movable section insertion hole, so that the pressing mechanism presses the protrusion section against the port facing surface by the plane at the tip end of the movable section by relatively rotating the movable section with respect to the block main body and displacing the movable section in an insertion direction into the movable section insertion hole.

4. The flow channel module according to claim 1, wherein a positional relationship between a terminal end wall surface at a deepest position inside the concave section and an end portion of the connection flow channel on a side of the port facing surface corresponds to a positional relationship between a terminal end portion of the protrusion section and the port, and is set so that positioning between the connection flow channel and the port is performed when the terminal end portion of the protrusion section that is inserted into the concave section comes into contact with the terminal end wall surface of the concave section.

5. The flow channel module according to claim 1,
wherein a ring sealing member having a through hole at a position corresponding to the port is sandwiched between the port of the protrusion section and the port facing surface, and
wherein a concave section having a same shape as the sealing member is provided at a position of the protrusion section where the sealing member is arranged.

6. The flow channel module according to claim 1, wherein the flow channel plate is made of metal.

7. The flow channel module according to claim 1, wherein a stationary phase for chromatogram separation is supported in the inner flow channel of the flow channel plate.

8. A gas chromatograph comprising:
an analytical column composed of the flow channel module according to claim 7;
a sample injection section connected to a port on an inlet side of the analytical column via a flow channel, for injecting a sample gas into the analytical column; and
a detector connected to a port on an outlet side of the analytical column via a flow channel, for detecting a sample component separated by the analytical column.

* * * * *